United States Patent
Nagashima et al.

[11] Patent Number: 5,094,786
[45] Date of Patent: Mar. 10, 1992

[54] METHOD AND APPARATUS FOR DETERMINATION OF INGREDIENTS OF TABLETS

[75] Inventors: Jiro Nagashima, Chiba; Masatoshi Utsunomiya, Narashino; Norimichi Suzuki, Chiba; Kazuhiko Nakamura, Hasuda, all of Japan

[73] Assignee: Lion Engineering Co., Ltd., Tokyo, Japan

[21] Appl. No.: 585,814

[22] Filed: Sep. 20, 1990

[30] Foreign Application Priority Data

Sep. 21, 1989 [JP] Japan .................................. 1-243435

[51] Int. Cl.⁵ ............................................. G01G 9/00
[52] U.S. Cl. ..................................... 264/40.2; 73/433; 73/865; 264/40.4; 425/140; 425/148
[58] Field of Search ............. 264/40.2, 40.4, 113, 264/40.1; 425/136, 140, 148, 353, 352; 73/433, 865

[56] References Cited

U.S. PATENT DOCUMENTS 3,836,299 9/1974 Houston et al. ................. 425/128
4,452,579 6/1984 Janson .............................. 425/140

Primary Examiner—Mary Lynn Theisen
Attorney, Agent, or Firm—Price, Gess & Ubell

[57] ABSTRACT

A tablet determining method and an apparatus therefor capable of accurately determining ingredients of a multi-layer tablet without breaking the tablet. A multi-layer tablet is lighted from light sources, an area of the side surface of the tablet on which a boundary line between the layers appears is detected by image processing, an area of the side surface of at least one of the layers of the tablet which are separated by the boundary line is detected by image processing, and data obtained by the image processing and data on the total weight of the tablet are used for determining the layer by processing.

22 Claims, 16 Drawing Sheets

FIRST STATION

SECOND STATION

THIRD STATION

METHOD AND APPARATUS FOR DETERMINATION OF INGREDIENTS OF TABLETS

BACKGROUND OF THE INVENTION

The present invention relates to a tablet determining method and an apparatus therefor, and more particularly, to a tablet determining method and an apparatus therefor which are adapted to determine ingredients of solid tablets used as medicines, foods, chemicals or the like.

In general, in the manufacturing of a tablet such as a medicine or the like, analysis of the tablet is highly significant in quality control. The determination of ingredients in the tablet is indispensable for ensuring the dose of the tablet.

Conventionally, both non-destructive and destructive tests have been employed for this purpose. The non-destructive test is adapted to measure the weight of the tablet, its diameter, its thickness and the like without breaking it and the destructive test is adapted to measure the properties of the tablet through destruction of the tablet such as fracture, melting or the like. Various tests are carried out separately or successively through a manual operation.

A tablet machine for manufacturing a single-layer tablet is automatically controlled by merely weighing the tablet continuously. However, for a multi-layer tablet comprising a plurality of layers with different gradients for each layer, it is impossible to measure each ingredient. Thus, a troublesome method such as chemical analysis, gas chromatography, liquid chromatography or the like is required for determining the ingredients of the layers of the tablet. For example, the amount of aspirin in a tablet is determined by crushing the tablet, dissolving it in ethyl alcohol to prepare a solution and adding sodium methoxide to the solution to determine the amount of methoxide consumption in the presence of an indicator. The amount of aspirin to be charged in the tablet is manually adjusted depending upon the thus-determined aspirin.

In the manufacturing of such a tablet, it is highly desirable to rationalize the tablet making process and to increase the production capacity. For this purpose, the unmanned automatic operation of the tablet machine is demanded. In order to satisfy such a demand, it is required to accomplish automatic adjustment of the tablet machine. However, as described above, a troublesome method such as liquid-chromatography, chemical analysis or the like which requires much labor and time is required for quality control of the tablet. Even use of an automatic analyzer requires as much as ten minutes or more to analyze one sample (two or three tablets). Also, such an automatic analyzer still requires labor.

SUMMARY OF THE INVENTION

The present invention has been made in view of the foregoing disadvantages of the prior art.

Accordingly, it is an object of the present invention to provide a tablet determining method which is capable of permitting the time required for a tablet making operation to be significantly decreased.

It is another object of the present invention to provide a tablet determining method which is capable of rapidly and accurately determining the ingredients of a multi-layer tablet without manual operation.

It is a further object of the present invention to provide a tablet determining method which is capable of accurately determining the ingredients of a multi-layer tablet without breaking the tablet.

It is still another object of the present invention to provide a tablet determining method which is capable of continuously and automatically determining the ingredients of a multi-layer tablet.

It is another object of the present invention to provide a tablet determining method which is capable of not only continuously and automatically determining the ingredients of a multi-layer tablet but feedback-controlling the amount of the ingredients to be fed for preparing the tablet, depending upon the determination of the ingredients.

It is yet another object of the present invention to provide a tablet determining apparatus which is capable of permitting the time required for a tablet making operation to be significantly decreased.

It is even another object of the present invention to provide a tablet determining apparatus which is capable of rapidly and accurately determining the ingredients of a multi-layer tablet without manual operation.

It is a still further object of the present invention to provide a tablet determining apparatus which is capable of accurately determining the ingredients of a multi-layer tablet without breaking the tablet.

It is a yet further object of the present invention to provide a tablet determining apparatus which is capable of continuously and automatically determining the ingredients of a multi-layer tablet.

It is another object of the present invention to provide a tablet determining apparatus which is capable of not only continuously and automatically determining ingredients of a multi-layer tablet but feedback-controlling the amount of the ingredients to be fed for preparing the tablet, depending upon the determination of the ingredients.

In accordance with one aspect of the present invention, a tablet determining method is provided. The method comprises the steps of weighing a tablet to detect a weight $W_0$ of the tablet, taking an image of the whole side edge or surface of the tablet to measure a side edge or surface area $A_0$ of the tablet, taking an image of the side surface of a layer of at least one predetermined component of the tablet to measure a side surface area $A_1$ of the layer, and obtaining a weight $W_1$ of the predetermined component according to a predetermined formula using the weight $W_0$, whole side surface area $A_0$ and side surface area $A_1$.

In a preferred embodiment of the present invention, the formula is $$W_1 = B_0 + B_1 A_1 + B_2 A_0 + B_3 W_0$$

wherein $B_0$, $B_1$, $B_2$ and $B_3$ each are a parameter.

In a preferred embodiment of the invention, the method further comprises the step of controlling the amount of at least one of components of the tablet to be fed for preparing the tablet, depending upon the obtained weight of said predetermined component.

In accordance with another aspect of the present invention, a tablet determining apparatus is provided. The apparatus comprises a weighing means for weighing a tablet to detect a weight $W_0$ of the tablet and an image-taking means for taking an image of the whole side surface of the tablet to measure a side surface area $A_0$ of the tablet. The image-taking means also takes an image of the side surface of a layer of at least one predetermined component of the tablet to measure a side surface area $A_1$ of the layer. The apparatus further comprises a processing means for obtaining a weight $W_1$ of the predetermined component according to a predetermined formula using the weight $W_0$, whole side surface area $A_0$ and side surface area $A_1$.

In a preferred embodiment of the present invention, the apparatus further comprises a control means for controlling the amount of at least one of components of the tablet which are be fed for preparing the tablet, depending upon the obtained weight of the predetermined component.

The present invention constructed as described above is effectively applied to the determination the ingredients of a multi-layer tablet such as, for example, a two-layer tablet comprising two upper and lower layers. The two layers may comprise, for example, an upper aspirin layer made of 90% aspirin and 10% starch and a lower alkali granule one made of aluminum glycinate, magnesium oxide and the like. The aspirin layer is translucent and the alkali layer is opaque, so that when luminance of the aspirin layer is high while being lighted from above, a boundary line defined between the aspirin layer and the alkali layer may be distinctly observed. Therefore, when the tablet is lighted in order that an image of the side surface or edge of the tablet is taken through a camera, an area of the side surface of the aspirin layer and an area of that of the tablet are measured in order.

The so-measured surface area of the aspirin layer has a relationship to the content of aspirin in the tablet, so that the measuring of the surface area may lead to determination of the aspirin content. More specifically, it was proved that a correlation coefficient between the aspirin layer and the aspirin content is 0.903 for the whole data of 30 samples and 0.9998 for the mean value of data of 10 samples. The fact indicates that the relationship between the surface area of the aspirin layer and the aspirin content is linear. Also, a multiple regression analysis was carried out using data actually measured under the conditions that the weight of the aspirin layer is defined as $W_1$, and $A_1$, $A_0$ and $W_0$ respectively indicating the area of the aspirin layer, the whole area of the tablet and the whole weight of the tablet are selected as independent variables. As a result, $B_0=240$, $B_1=0.0487133$, $B_2=-0.0185115$ and $B_3=-0.1182358$ were obtained with respect to the following formula $$W_1 = B_0 + B_1 A_1 + B_2 A_0 + B_3 W_0 \tag{1}$$

A value of the weight $W_1$ of the aspirin layer which was actually calculated according to the formula (1) has an error as small as $-0.1$ to $+0.5\%$ with respect to a true value of the weight, resulting in the formula exhibiting high accuracy. Likewise, a calculated value of the weight of the alkali layer has an error as small as $-0.8$ to $+0.2\%$ with respect to its true value.

Thus, it was verified that the weight of the aspirin layer or alkali layer can be estimated with very high accuracy by carrying out operation or calculation using detected data on the area of each layer, the whole area of the tablet and the weight of the tablet.

The present invention permits a multi-layer tablet to be generally formed into a similar configuration according to such a process as described hereinafter using a punch and die combination, therefore, the above-described procedure can be substantially applied to tablets different in ingredients, hue or the number of layers. For example, in a tablet with layers different in hue, the area of a layer to be analyzed may be detected or measured by subjecting a difference in hue recognized through a filter to image processing. In a tablet of three or more layers, the area of a layer to be analyzed is measured by dividing the layers into the analyzed layer and the remaining layers and subjecting the analyzed layer to image processing.

The data obtained as described above are subject to operation according to the formula (1) described above by means of a computer, so that an ingredient of each layer may be instantaneously weighed. Then, each of the values thus produced is then compared with a standard value to obtain a deviation therebetween, which is then feed-backed to an ingredient feed rate control section of a tablet machine to control a feed rate of each ingredient, resulting in stable and accurate real-time control of the ingredients of the tablet being easily accomplished.

BRIEF DESCRIPTION OF THE DRAWINGS

These and other objects and many of the attendant advantages of the present invention will be readily appreciated as the same becomes better understood by reference to the following detailed description when considered in connection with the accompanying drawings in which like reference numerals designate like or corresponding parts throughout; wherein.

DETAILED DESCRIPTION OF THE PREFERRED EMBODIMENTS

Now, the present invention will be detailedly described hereinafter with reference to the accompanying drawings.

Figure 1:
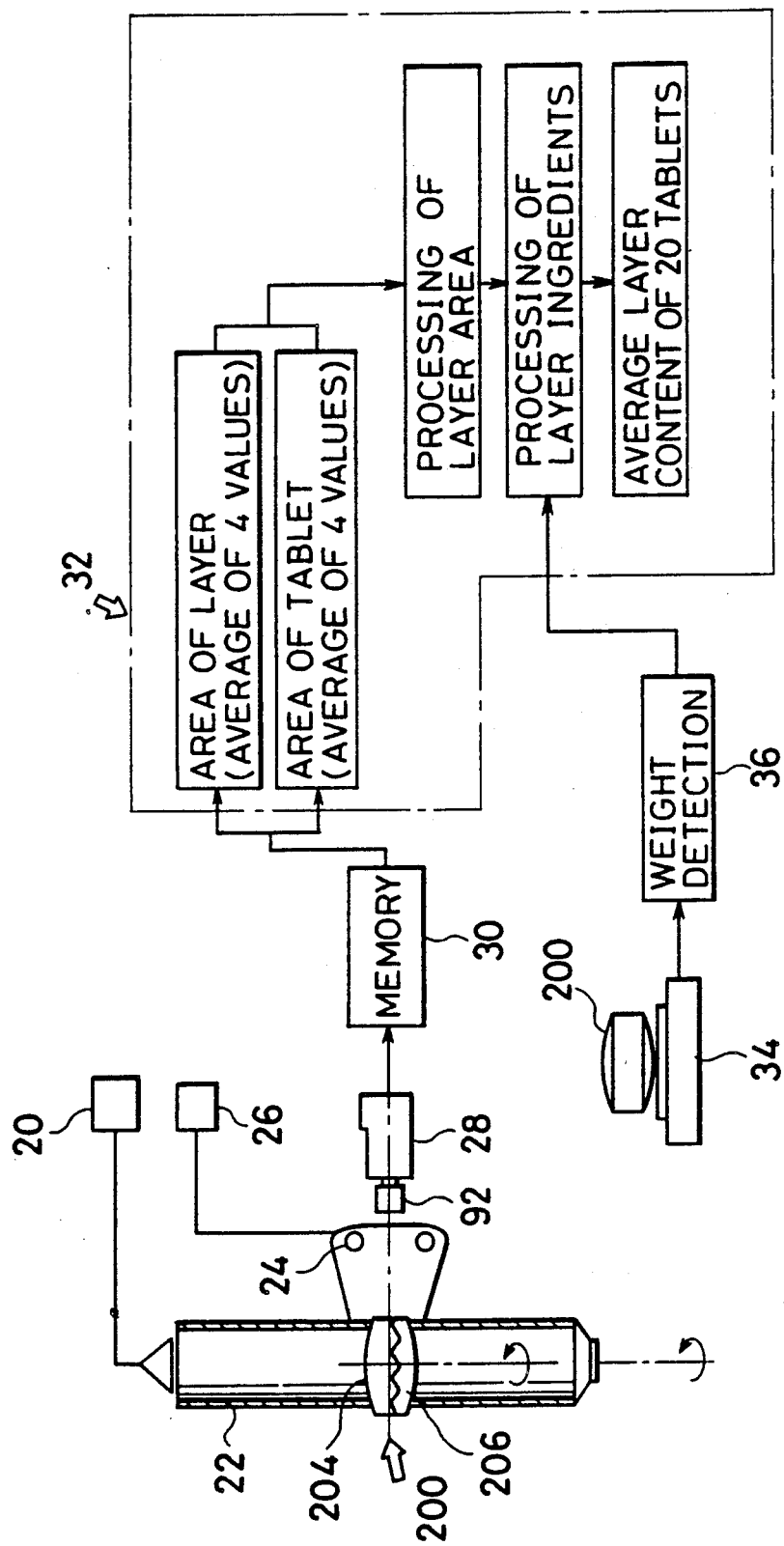
FIG. 1 is a flow chart generally showing a process of the present invention.
Figure 2:
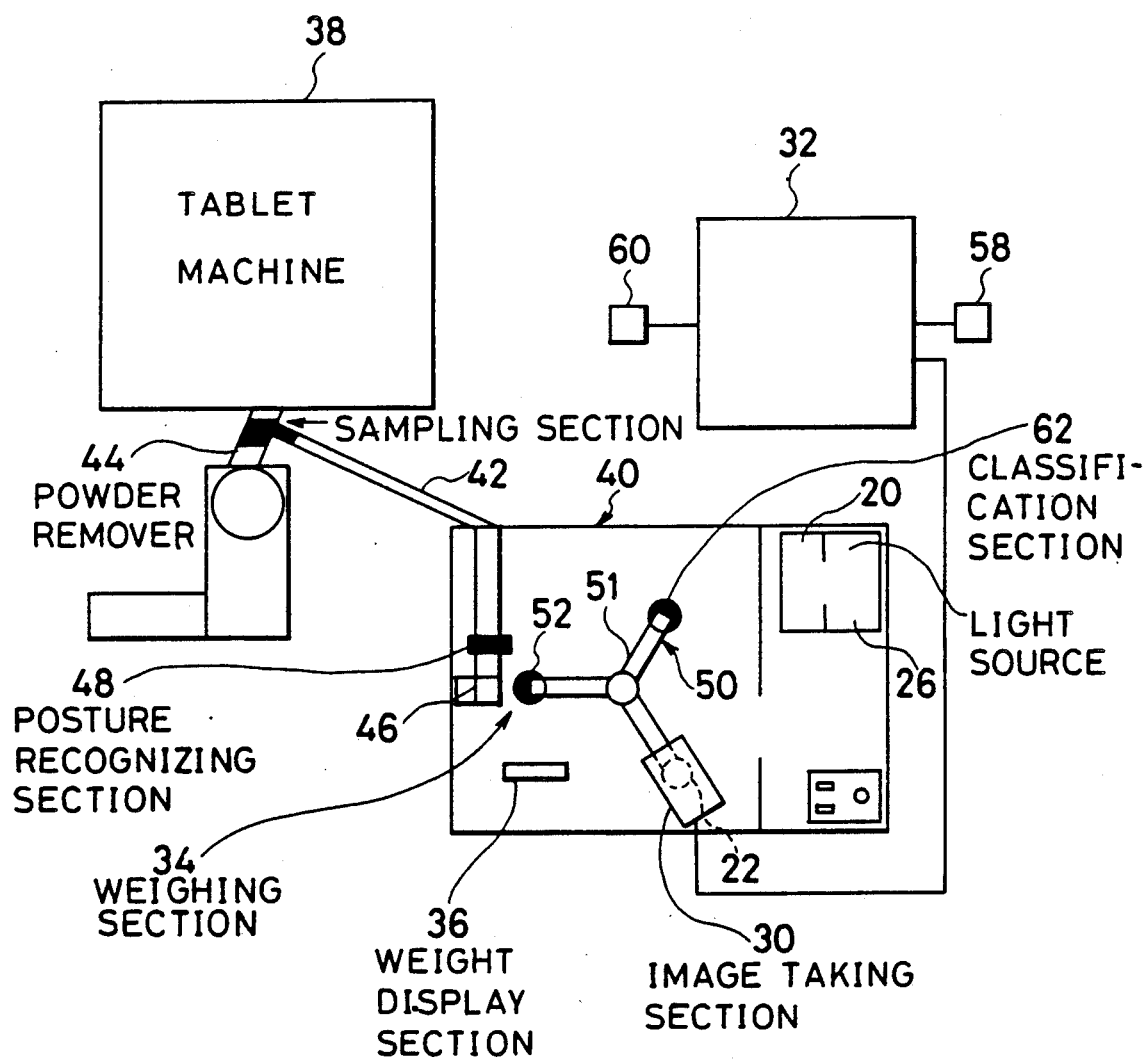
FIG. 2 is a block diagram generally showing an embodiment of a tablet determining apparatus according to the present invention.
Figure 3:
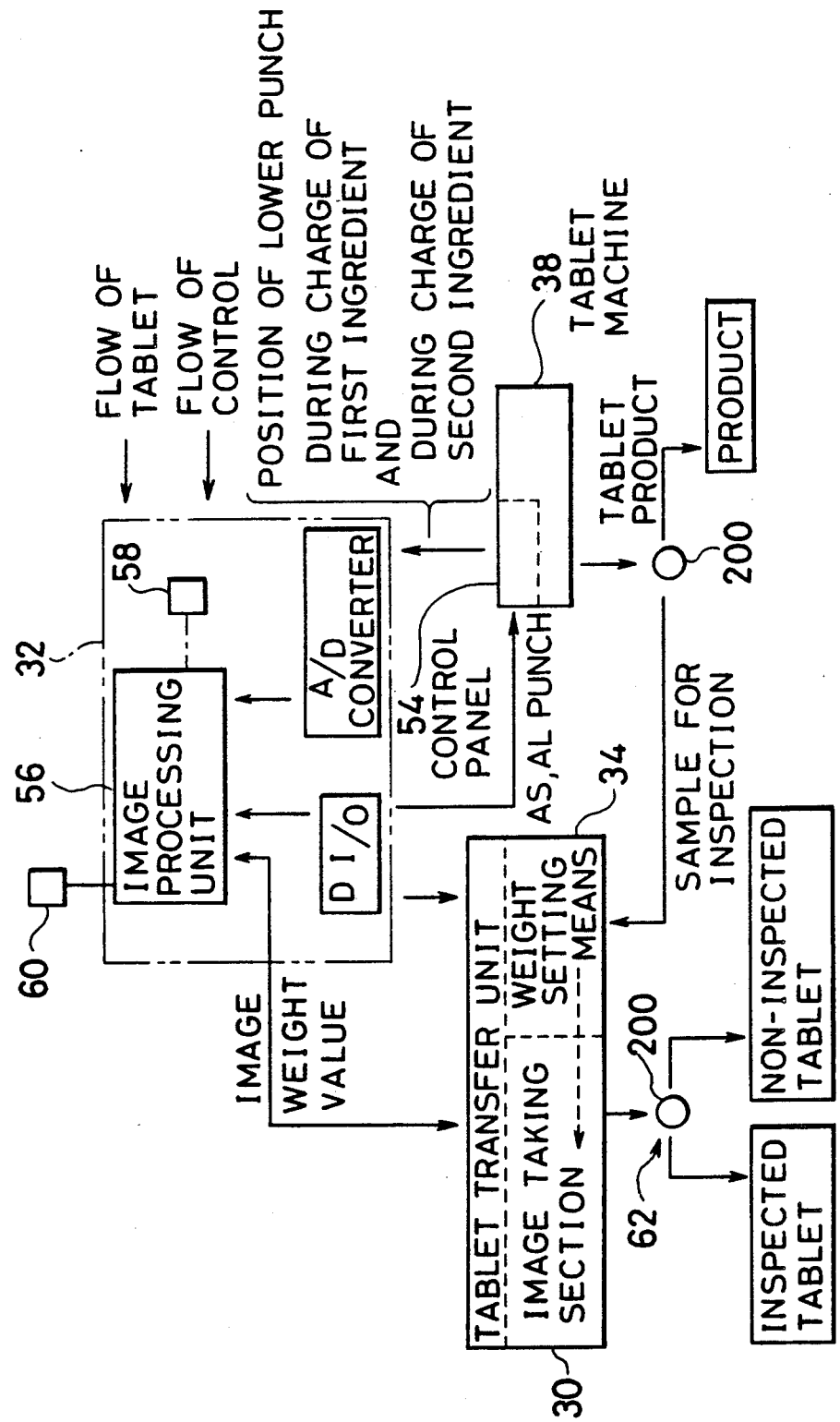
FIG. 3 is a block diagram showing an image processing unit incorporated in the tablet determining apparatus shown in FIG. 2.
Figure 4:
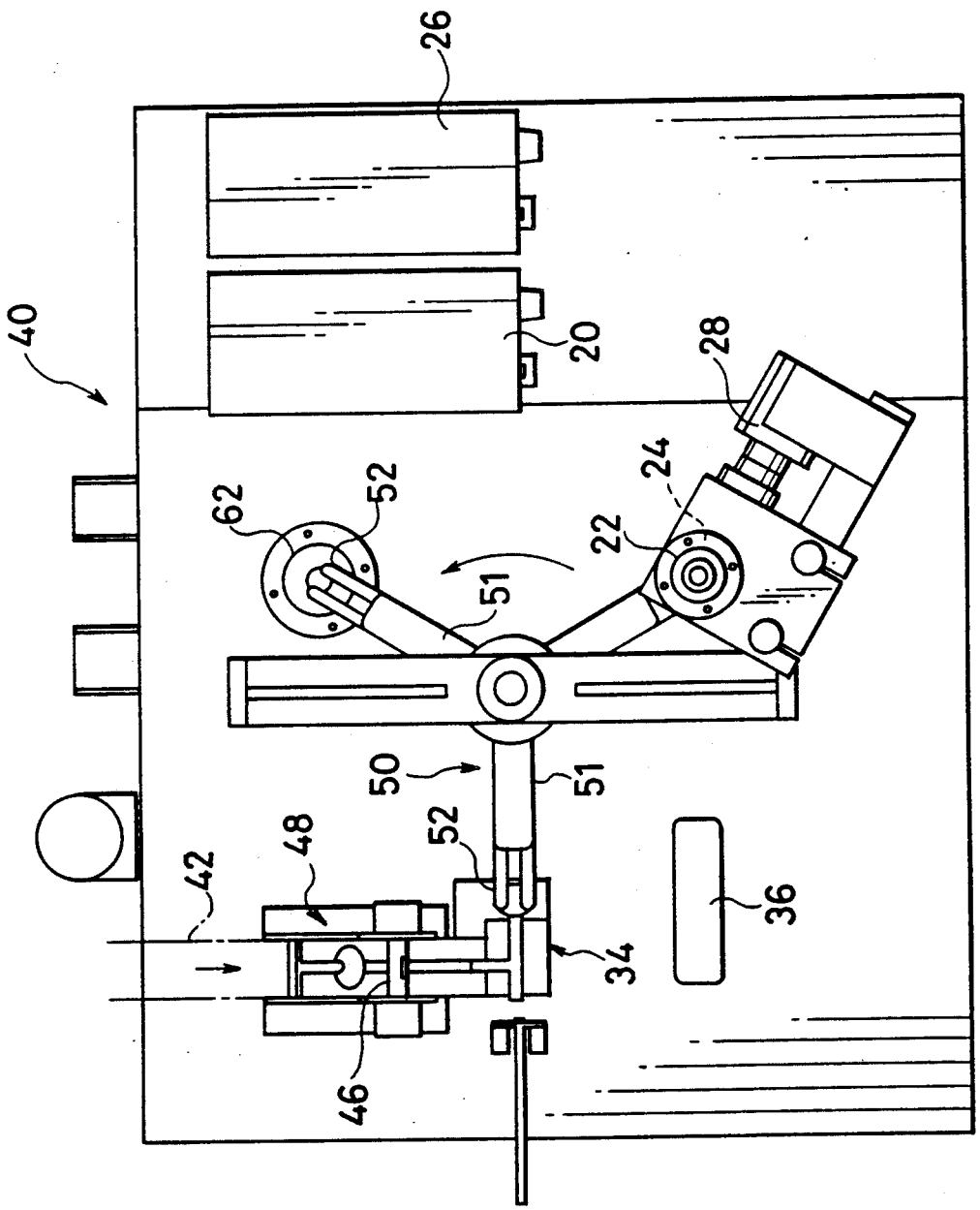
FIG. 4 is a plan view showing a tablet transfer and inspection unit in the tablet determining apparatus of FIG. 2.
Figure 5:
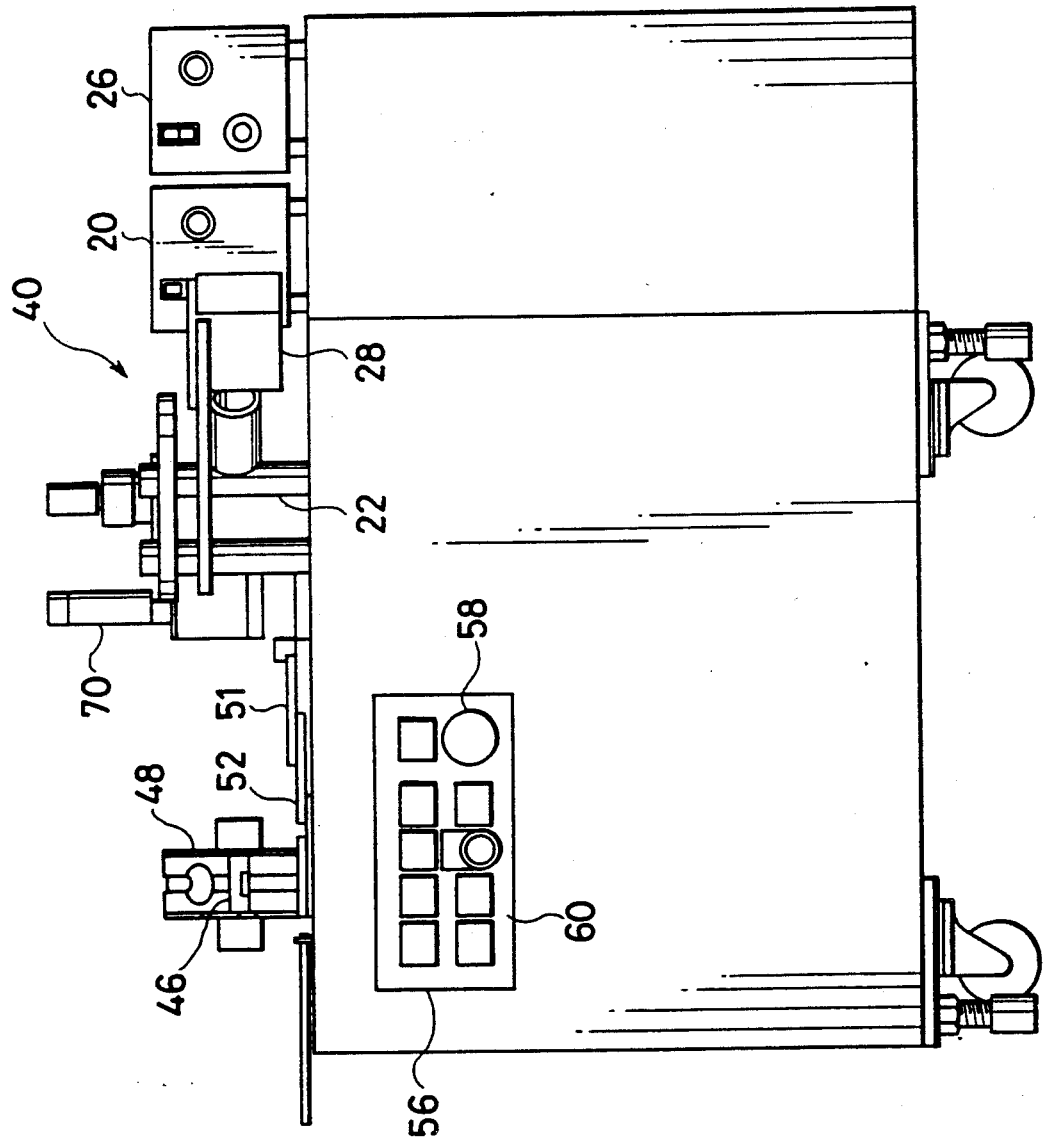
FIG. 5 is a side elevation view of the tablet transfer and inspection unit shown in FIG. 4.

FIGS. 1 to 3 generally show an embodiment of the present invention which is constructed so as to determine ingredients of a solid tablet 200 comprising two layers or an upper aspirin layer 204 and a lower alkali layer 206 vertically combined together. In general, in the illustrated embodiment, the upper surface of the aspirin layer 204 of the tablet 200 is downwardly lighted from a light source 20 through a lighting tube 22, so that the light is then laterally discharged through the side surface of the aspirin layer 204. Subsequently, the side edge or surface of the solid tablet 200 is laterally lighted from a ring lamp 24 connected to a light source 26, so that both a side surface or edge area of the aspirin layer on the side of the tablet 200 on which a boundary between the two layers appears and which is observed through a camera 28 of an image taking section 30 and a side edge or surface area of the tablet which is observed through the camera 28 may be measured through the camera 28. The thus-measured data are then supplied through the image taking section 30 to a computer of an image processing unit 32, in which the data are processed. Also, the total weight of the tablet 200 is measured at a weighing section 34, which may comprise, for example, an electronic balance, and is displayed at a weight display section 36. Also, the data on the thus-measured weight are supplied to the image processing unit 32. Thus, the measured weight of the tablet 200 and the measured areas of the tablet and aspirin layer 204 are subject to processing in the image processing unit 32, resulting in the weight of the aspirin layer 204 being obtained.

In the illustrated embodiment, the processing is preferably carried out by taking and storing a plurality of area images of the side surface of the whole tablet 200 and a plurality of area images of the side surface of the aspirin layer 204 made of a light-permeable aspirin ingredient through the camera 28 into the image taking section 30 while varying the relative position of the camera 28 with respect to the side surface of the tablet 200 and aspirin layer 204 and detecting the average number of pixels (an average value obtained through several operations) on a memory in the image taking section 30.

The solid tablets 200 are automatically sampled while being discharged from a tablet machine 38. The sampled tablets each are weighed and then lighted from a halogen lamp or tungsten lamp, so that images of the side surface of the tablet on which the boundary line between the aspirin layer 204 and the alkali layer 206 constituting the layers is defined as a separating line may be taken through the camera 28. Data of the so-obtained images are supplied to the image processing unit 32, wherein the microcomputer carries out the image processing and operation to compute the weight of each ingredient of the tablet. The so-obtained weight is feed-backed to the tablet machine 38, so that the amount of materials or ingredients for the aspirin layer and alkali layer to be charged respectively in the tablet machine may be controlled as desired.

The tablet determining apparatus of the illustrated embodiment also includes a tablet transfer and inspection unit generally indicated at reference 40, which includes a sampling chute 42 connected to a discharge passage 44 of the tablet machine 38 through which the tablets produced are discharged from the tablet machine 38. The sampling chute 42 is connected to the discharge passage 44 in a manner to branch off from the discharge passage 44 and provided with an intake shutter (not shown) and a stopper (not shown), which are adapted to be operated by means of an air cylinder means. The tablet transfer and inspection unit 40 also includes a tablet reversing mechanism 46 which includes a tablet posture recognizing section 48 for judging whether the tablet is being fed to the tablet transfer and inspection unit 40 while being kept at a correct posture. When the tablet is upside down, the posture recognizing section 48 detects such an incorrect posture of the tablet, so that the tablet reversing mechanism 46 reverses the tablet 200. For this purpose, the posture recognizing section 48 may be constructed in such a manner that the vertical position of the boundary line between the aspirin layer 204 and the alkali layer 206 is detected through a laser sensor, resulting in recognizing whether the tablet is placed in a correct posture. Alternatively, the posture of the tablet may be recognized by detecting a depression such as a marking, a stamp or the like formed on the upper surface of the aspirin layer 204.

The tablet transfer and inspection unit 40 further includes a tablet transfer mechanism 50 which includes a tablet rotating chuck arm means 51 and a tablet chuck and release means 52 for transferring the tablet from the tablet reversing mechanism 46 to tablet inspection positions. Further, the unit 40 includes a control panel 54 for controlling the position of pestles of the tablet machine 38 depending upon a signal fed from the image processing unit 32. For this purpose, the control panel 54 is electrically connected to the image processing unit 32 and may include a rotation arm or belt conveyor.

In the illustrated embodiment, the light sources 20 and 26, lighting tube 22, ring lamp 24, image taking section 30, weighing section 34 and weight display section 36 constitute a part of the table transfer and inspection unit 40.

The image processing unit 32, as shown in FIG. 3, may include a data processing section 56 adapted to automatically process a side surface area of at least one ingredient layer of the tablet 200 such as, for example, the aspirin layer 204 and a side surface area of the whole tablet 200, a display section 58 for recording and displaying the data processed by the data processing section 56, and a setting section 60 to which conditions for determining the tablet are input. In the illustrated embodiment, the so-constructed image processing unit 32 is adapted to carry out binary processing of images of the tablet and aspirin fed through the camera 28 thereto to compute the side surface area of the aspirin layer, as well as the side surface area of the tablet.

Of the tablets discharged from the tablet machine 38, a predetermined number of tablets (for example, twenty tablets) are fed through the sampling chute 42 to the tablet transfer and inspection unit 40 and the average of detected values of the tablets is utilized as data for one inspection.

The tablet transfer and inspection unit 40, as shown in FIGS. 4 to 8, is adapted to recognize the vertical posture of the tablet 200 at the posture recognizing section 48, feed the tablet to the weighing section 34 while maintaining it at a predetermined posture, feed data on the weight of the tablet to the image processing unit 32, and feed the tablet to the image taking section 30 by means of the rotating chuck arm means 51 of the tablet transfer mechanism 50. In the image taking section 30, the tablet 200 is lighted from the light source and ring lamp 24 and the camera 28 takes images of the side surface of each of the tablet and the aspirin layer 204 at four different positions. An image signal of the so-obtained images is then fed to the image processing unit 32.

Then, the tablet 200 is fed to a tablet classification section 62 through the rotating chuck arm means 51.

Figure 6:
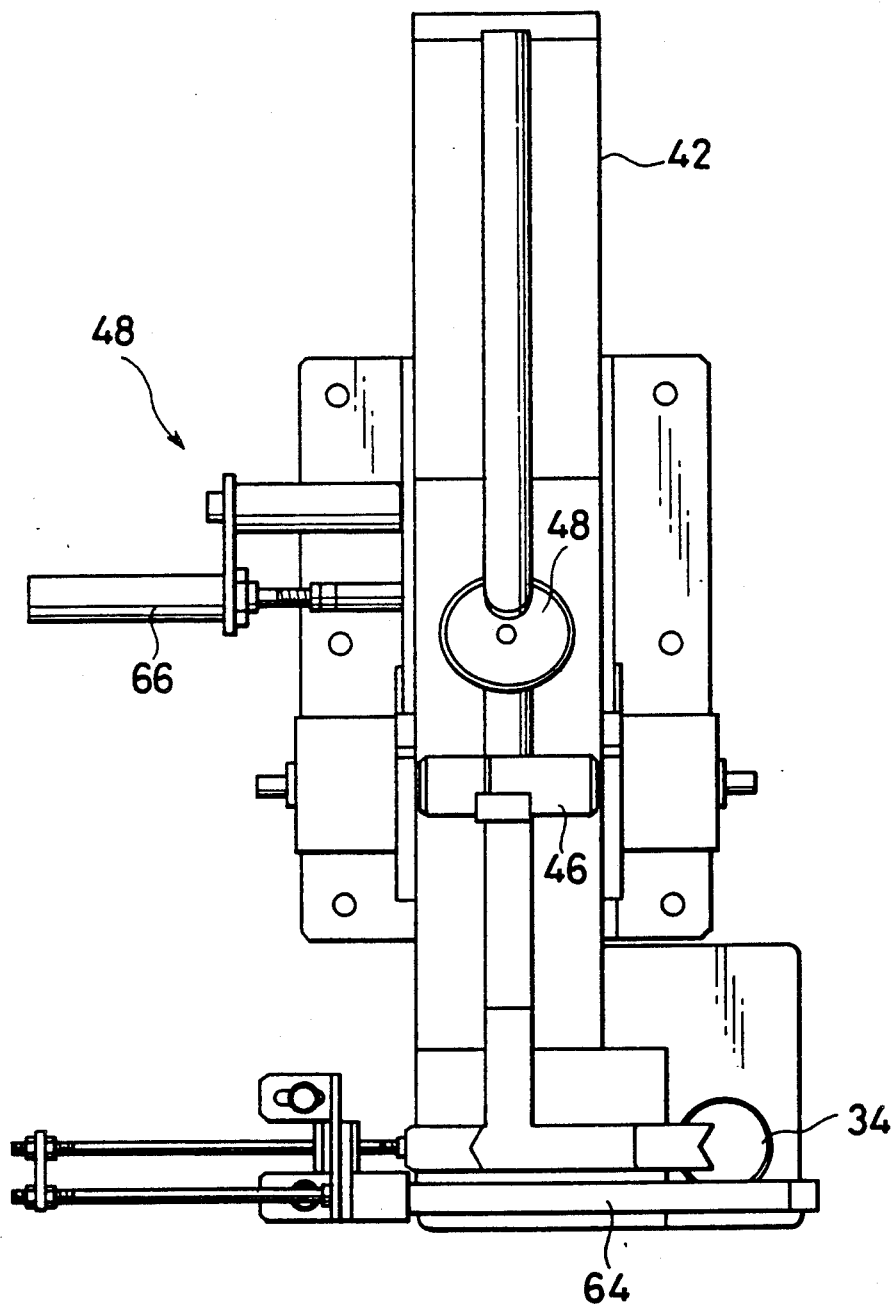
FIG. 6 is a plan view showing a tablet posture recognizing section.
Figure 7:
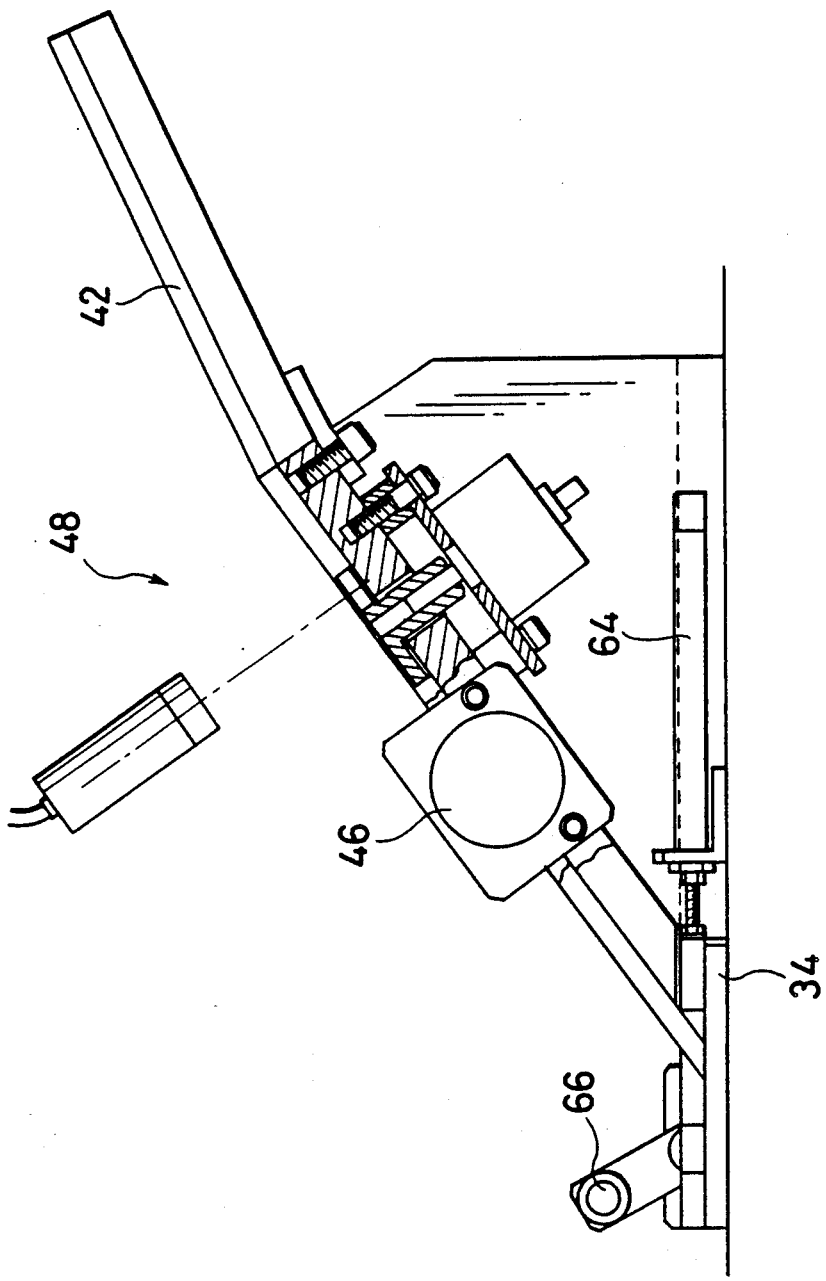
FIG. 7 is a side elevation view of the tablet posture recognizing section.
Figure 8:
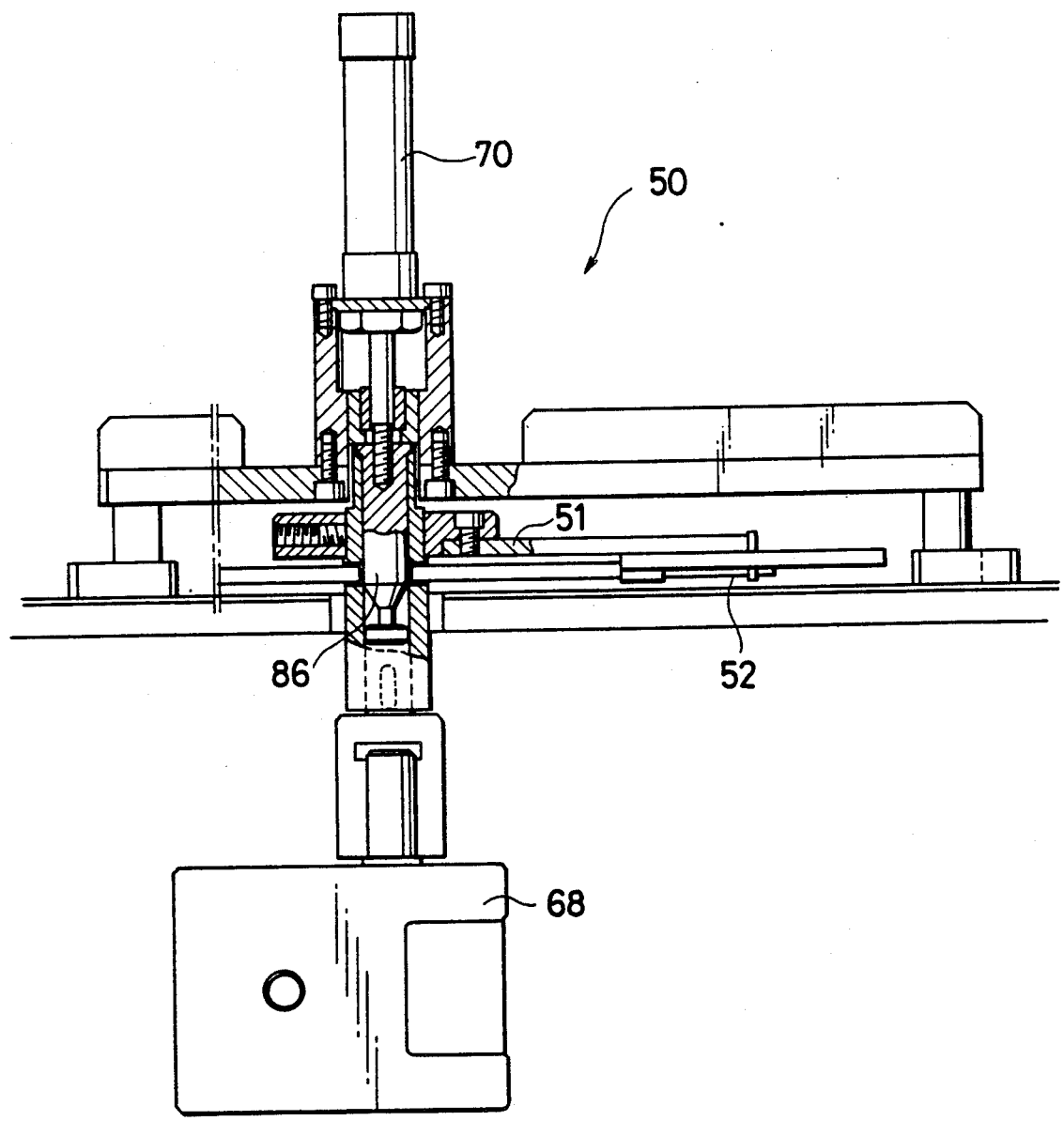
FIG. 8 is a side elevation view partly in section showing a tablet transfer unit.

The weighing section 34, as shown in FIGS. 6 and 7, is adapted to put the tablet on an electronic balance by means of air cylinders 64 and 66 to weigh it. The electronic balance may be used which has a weighing range of 0 to 110 g, a weighing accuracy of 0.001 g and a stabilizing time of about 2 seconds and is of the double-interface type. In the illustrated embodiment, three such chuck arm means 51 are arranged at angular intervals of 120 degrees through an index means 68. Also, three chuck and release means 52 are respectively provided at the distal ends of the three chuck arm means 51 and each are actuated by means of an air cylinder 70. Thus, in the tablet transfer mechanism 50, the chuck and release means 52 releasably hold the tablet in turn and the rotating chuck arm means 51 transfer it to the weighing section 34 and separating section 62 in turn. The index means 68 may be driven through an electromagnetic clutch and a reducer by means of a speed control motor.

Figure 9:
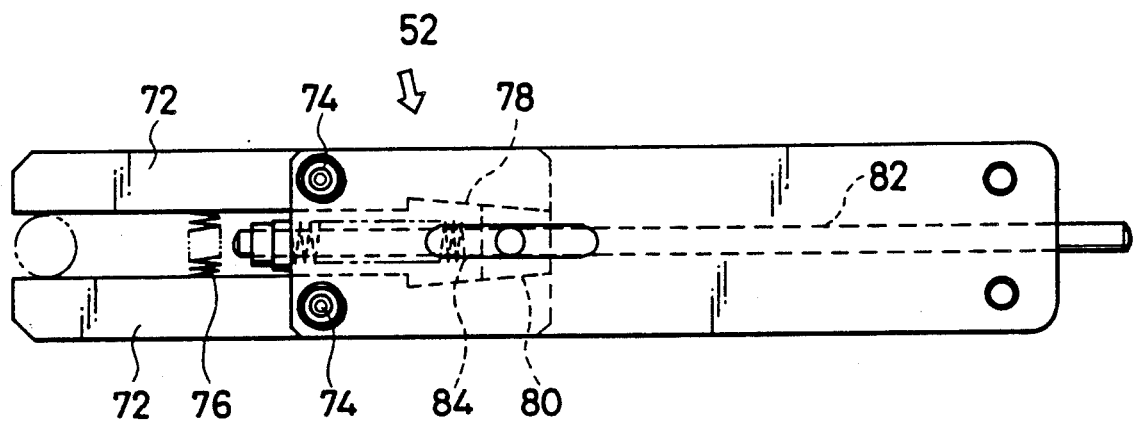
FIG. 9 is a plan view showing a tablet chuck and release means.

The tablet chuck and release means 52, as shown in FIG. 9, each include a pair of holding members 72 arranged opposite to each other and pivotally supported on support pins 74 and a spring 76 interposedly arranged between the holding members 72 in proximity to the distal ends of the members 72. The holding members 72 have tapered cam portions 78 formed on the inner surfaces of the proximal ends thereof opposite to each other. The tapered cam portions 78 are arranged in a manner to be opposite to each other. Between the tapered cam portions 78 is slidably fitted a slide member 80, which is arranged so as to be forcibly slid by means of a rod 82 against a spring 84 to open the holding members 72, resulting in the tablet 200 being releasably held thereon. The operation of each of the means 52 is controlled by moving a piston 86 actuated by the air cylinder 70.

Figure 10:
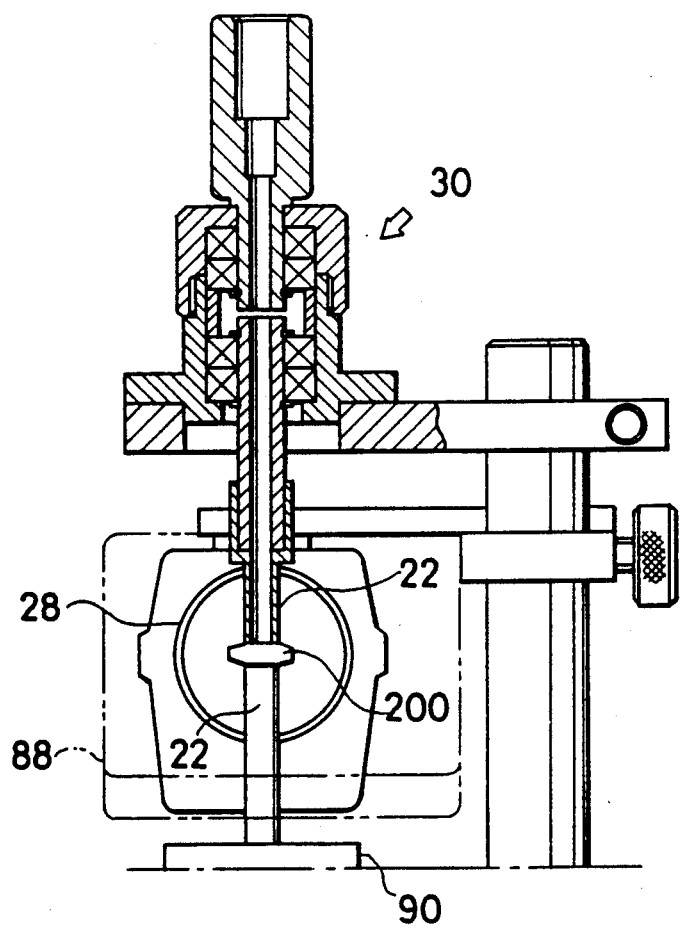
FIG. 10 is a front elevation view partly in section showing a tablet image taking section.
Figure 11:
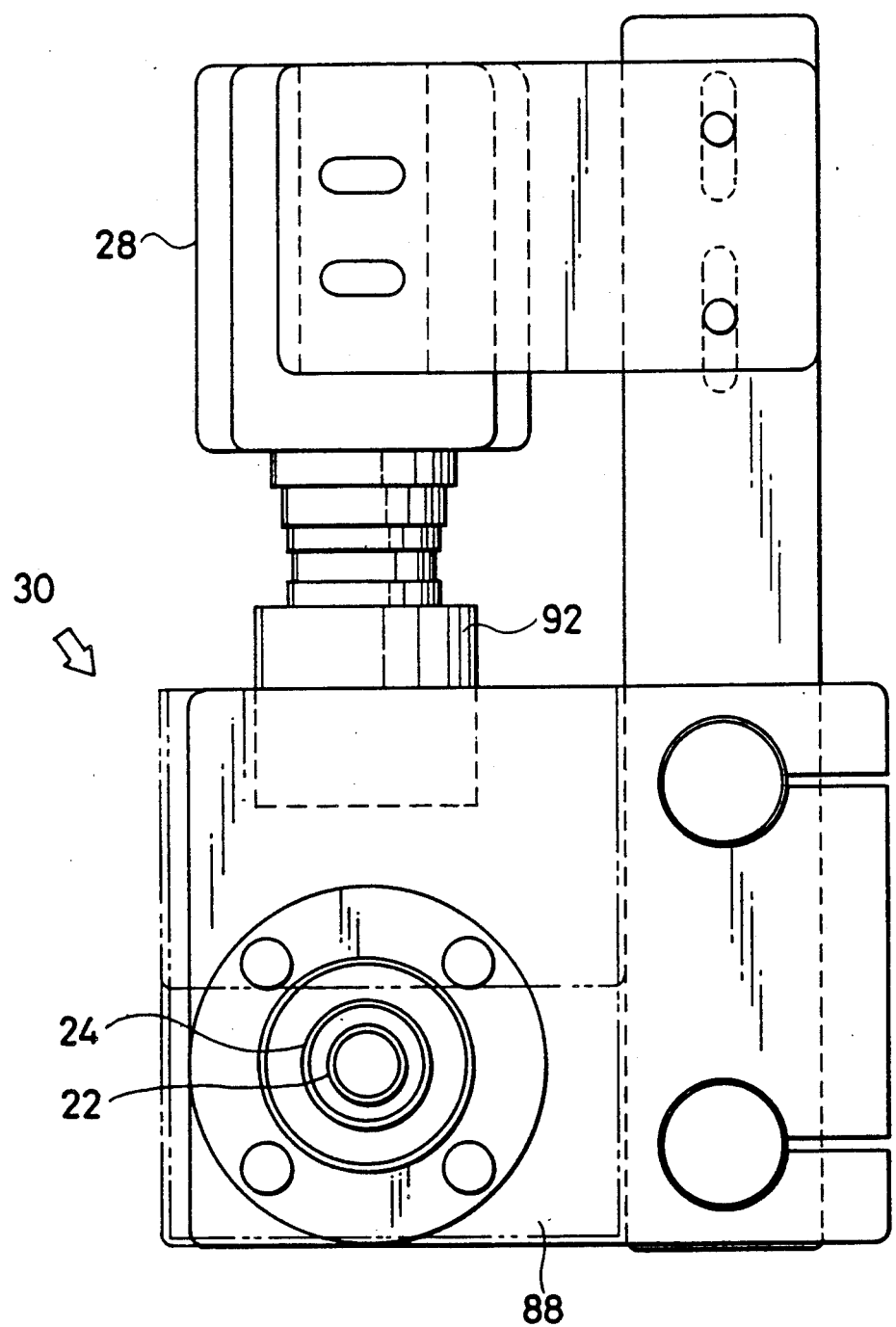
FIG. 11 is a plan view of the tablet image taking section.
Figure 12:
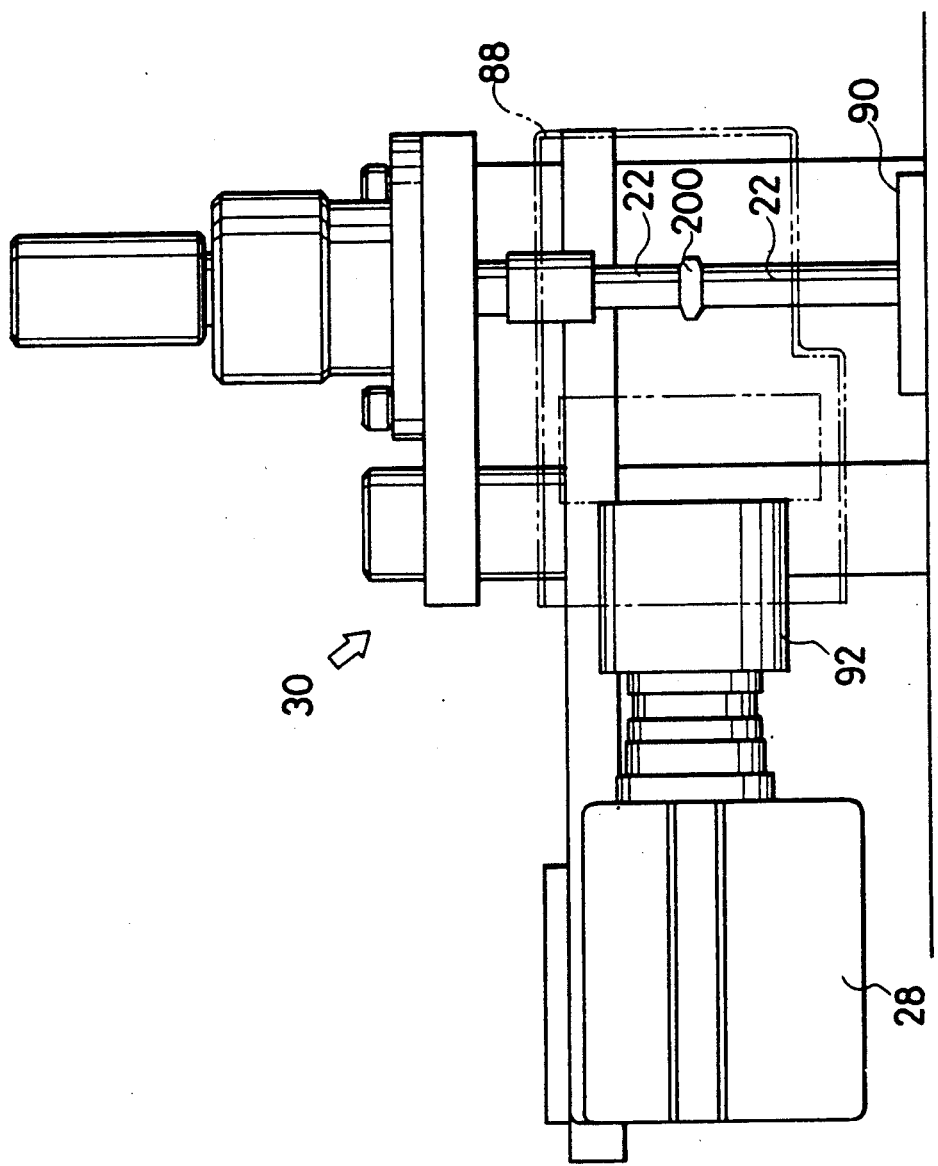
FIG. 12 is a side elevation view of the tablet image taking section.

In the image taking section 30, as shown in FIGS. 10 to 12, the tablet 200 put on a tablet support by means of the chuck arm means 51 is interposedly held between the lighting tubes 22 vertically arranged in a box 88 serving as a dark room by means of a tablet vertical moving means 90. Then, the tablet 200 is rotated while facing a lens 92 of the camera, so that images of the side surface of the whole tablet 200 and images of the side surface of the aspirin layer 204 may be taken at four different positions in the horizontal direction. The rotation of the tablet 200 is carried out through a stepping motor. A driving pulse is fed from the image processing unit 32 and the lighting on the tablet 200 is carried out through a lighting lamp using an optical fiber. In the illustrated embodiment, the ring lamp 24 is used for measuring the side surface area of the whole tablet and the lighting tube 22 is used for measuring the side surface area of the aspirin layer 204. The lighting tube 22 and ring lamp 24 each may be provided therein with an electromagnetic shutter adapted to operate depending upon a signal from the image processing unit 32. In order to prevent powders of the tablet 200 from adhering to the tablet support and the lighting tube 22, a suction line (not shown) may be arranged which is connected to a vacuum pump.

The tablet classification section 62 functions to classify a tablet as being normal or abnormal depending upon the results of weight measuring and image processing of the tablet.

The tablet determining apparatus of the illustrated embodiment includes an electric control section, which may include, in addition to a sequencer for controlling the tablet transfer and inspection unit 40, a speed controller, a stepping motor driver, a sensor amplifier for recognizing the posture of the tablet 200, a comparator, a transformer, a relay and the like, so that transmission of a signal between the image processing unit 32 and the sequencer causes an inspection cycle of the transfer and inspection unit 40 to be automatically carried out. Also, the tablet determining apparatus is so constructed that data on each of the tablets, its binary image, its weight, an estimate of its aspirin content, its standard deviation, the width of the deviation, the state of control of the punch of the tablet machine, a graph indicating a change in the average of weight and aspirin content of the tablet, any accident and the like, as well as a live image of the tablet and an inspection window may be displayed on a monitor unit.

Also, the image processing unit 32 is adapted to carry out processing of signals indicating the weight and image of the tablet, to thereby estimate the content of aspirin in the tablet. The image processing unit 32 compares the thus-obtained inspection results with reference data, to thereby optimum control the position of a punch for each of the first or aspirin layer 204 and the second or alkali layer 206 of the tablet 200. Further, in the tablet determining apparatus, the operation of the tablet transfer and inspection unit 40 is controlled through signal transmission between the image processing unit 32 and the sequencer, and inspection data, any accident of the transfer and inspection unit 40 and inspection data fed to a printer are displayed on the monitor unit.

Figure 13:
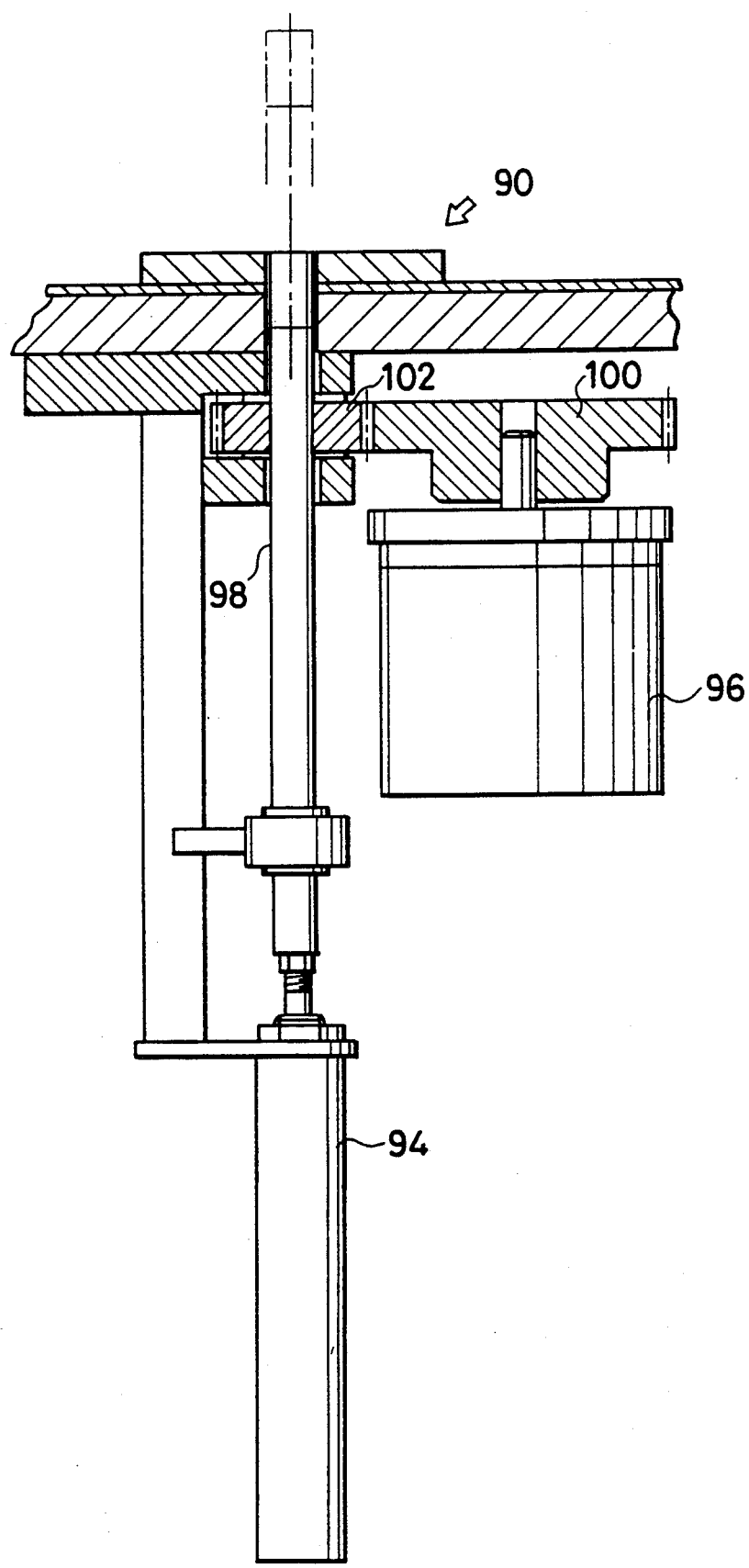
FIG. 13 is a side elevation view partly in section showing a mechanism for vertically moving and rotating a tablet.

The means 90 for vertically moving the tablet 200, as shown in FIG. 13, is vertically moved through a cylinder 94 and is adapted to transmit rotation of a step motor 96 to a support rod 98 through gears 100 and 102, to thereby rotate the tablet.

Figure 14:
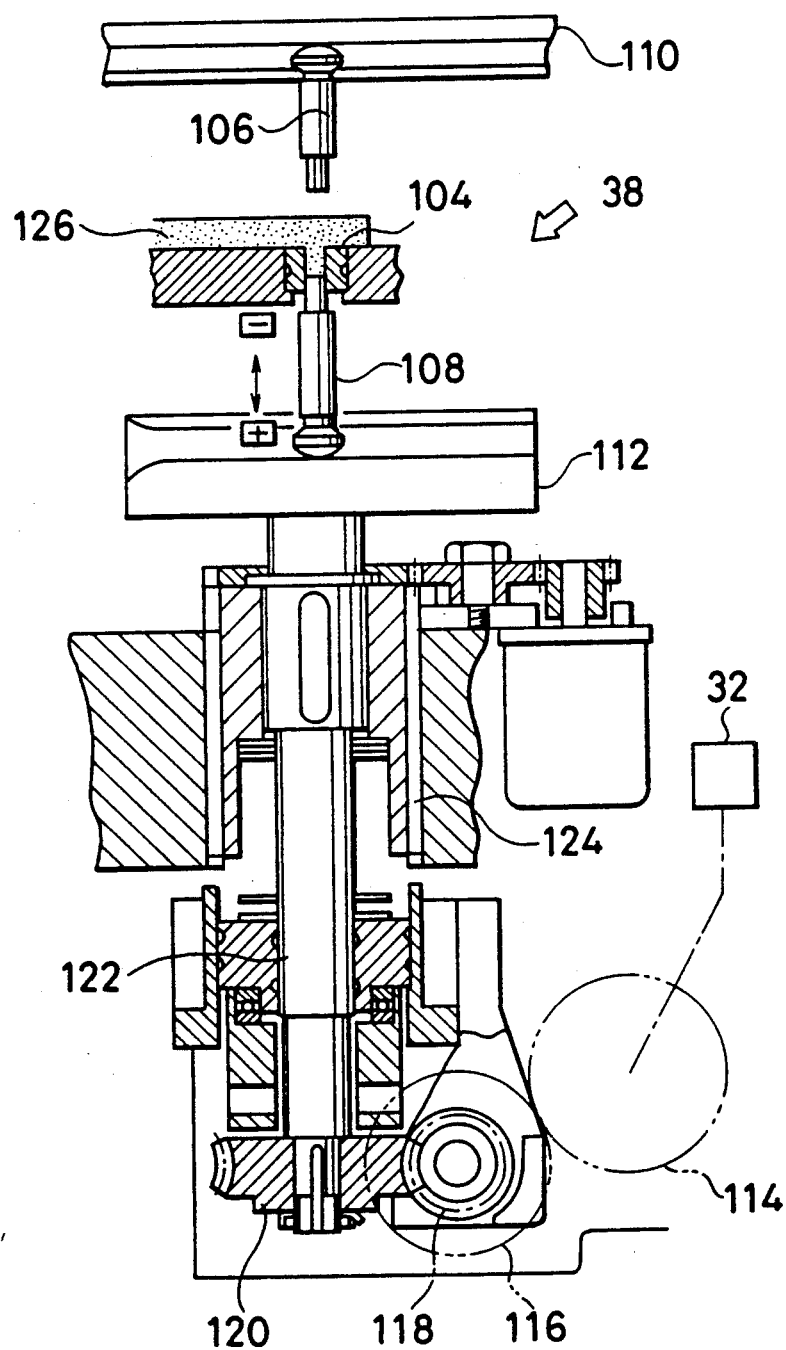
FIG. 14 is a side elevation view partly in section showing a tablet machine.

The tablet machine 38, as shown in FIG. 14, includes a die 104 which is charged with powders for ingredients of the tablets, an upper punch 106 and a lower punch 108 and is adapted to form the powders into a tablet through the die 104 and punches 106 and 108 while moving the powders between upper and lower rails 110 and 112. The amount of powders charged in the die 104 is adjusted by controlling the vertical position of the lower rail 112 by means of a lifting mechanism including a motor 114, as well as components 116, 118, 120, 122 and 124. The formation of the tablet will be more detailedly described hereinafter with reference to FIGS. 17A to 19C.

The manner of automatic operation of the tablet determining apparatus of the illustrated embodiment which is arranged in combination with the so-constructed tablet machine 38 will be described hereinafter.

A selection switch of the tablet transfer and inspection unit 40 is set at an automatic mode, and then information required for operating the unit 40 is input thereto through a keyboard of the setting section 60 of the image processing unit 32 and the unit 32 generates an inspection start command, resulting in the tablets being fed to the transfer and inspection unit 40 and subject to automatic measuring or inspection in the unit 40. More particularly, when the intake shutter of the sampling chute 42 is open, of the tablets discharged from the tablet machine 38 to the passage 44, a predetermined number of the tablets (for example, twenty tablets) are fed to the sampling chute 42. Then, when a sensor (not shown) provided on the chute 42 detects the completion of feeding of the tablets to the chute 42, the intake shutter and tablet stopper of the chute 42 are closed and open for a predetermined period of time (for example, for one minute), respectively, and the tablets each are transferred to the posture recognizing section 48. Then, the posture inspection of the tablet is carried out by measuring the vertical length of at least one of the layers of the tablet by means of the laser sensor and concurrently the zero setting of the weighing section 34 is carried out without the tablet. Also, the chuck arm means 51 is rotated 120 degrees to obtain correction data on the adhesion of tablet powders to the lighting tube 22 and tablet support.

After the posture of each of the tablets is thus inspected, the tablets are separately fed to the tablet reversing mechanism 50 in turn, wherein the tablet of a wrong posture is reversed so as to place the aspirin layer up. Then, the tablet is fed to the weighing section 34 by means of an air cylinder pusher, wherein the tablet is weighed. Data on the so-measured weight are fed to the image processing unit 32 after the measured value is stabilized.

Then, the tablet 200 is held on the chuck arm means 51, which is then rotated 120 degrees to bring the tablet 200 to the tablet support of the image taking section 30. The tablet support is upwardly moved through the tablet vertically moving means 90 by means of the air cylinder 94, to thereby interposedly hold the tablet 200 between the lighting tubes 22. Then, the tablet 200 is rotated by driving the stepping motor 96.

Images of the tablet 200 are obtained through the camera 28 during the rotation of the tablet. More particularly, first the ring lamp 24 opens a shutter of the light source 26 to obtain images of the side surface of the whole tablet at four positions different in angle from each other by 90 degrees. Then, a shutter of the light source 20 is open, so that images of the side surface of the aspirin layer are obtained at four positions different in angle by 90 degrees in order through the camera 28. Then, the table support is downwardly moved by means of the vertically moving means 90 and the tablet 200 is held on the table chuck and release means 52. Then, the table rotating chuck arm means 51 is rotated 120 degrees to feed the tablet to the classification section 62. At the classification section 62, the tablet is classified into an acceptable group or a non-acceptable group depending upon the results of processing in the image processing unit 32. Thus, the tablets 200 each are successively fed to the weighing section 34, image taking section 30 and classification section 62 through three such chuck arm means 51 and such a feeding operation is repeated so long as the tablets are fed to the tablet transfer and inspection unit 40. When the inspection of all the tablets is completed, the operation of the transfer and inspection unit is automatically stopped. The image processing unit 32 carries out processing with respect to all the inspected tablets, so that an estimate of each of the aspirin content and the average weight is printed out and displayed on the monitor unit.

If the results of inspection of the tablets are out of control, the image processing unit 32 generates a signal for controlling the position of the pestles of the tablet machine 38 to optimum change the relative amount between the aspirin layer 204 and the alkali layer 206, resulting in a first inspection cycle being completed. The subsequent inspection cycles are carried out depending upon a command signal automatically generated from the image processing unit 32.

The tablet transfer and inspection unit 40 may be manually operated for the purpose of confirming the inspection cycle. This is carried out independent from the image processing unit 32. However, the weighing operation, image taking operation and tablet classification operation are not manually carried out because they are carried out depending upon a command from the image processing unit 32. The manual operation may be carried out by changing over the selection switch on the control panel of the transfer and inspection unit 40 to a manual mode.

The shutter of the sampling chute 42 is kept open for a period of time during which a sampling button on the control panel is pressed; so that sampling of the tablets through the sampling chute 42 may be carried out so long as the tablets are flowing through the discharge passage 44 from the tablet machine 38. When the sampling button is released, the shutter of the sampling chute is closed and concurrently the tablet stopper of the chute is open, so that the sampled tablets are fed to the tablet posture recognizing section 48 in order.

When a transfer and operation button on the control panel is pressed, the successive feeding of the tablets to the posture recognizing section 48 and weighing section 34 is carried out through the rotation of the chuck arm means 51 at angular intervals of 120 degrees. Such an operation is continued irrespective of the tablet. Also, the inspection operations at the respective sections are synchronized with each other; accordingly, when any accident such as clogging of the lighting tube with the tablet occurs, the operation at each of the sections is immediately interrupted. When the transfer and inspection unit is in a manual mode, the classification section 62 is set at a non-inspection unit.

The illustrated embodiment has been described with reference to the tablet determining apparatus for determining the ingredients of a tablet comprising two layers. However, the present invention may be applied to a multiple-layer tablet comprising three or more layers. Also, the present invention may be applied to a multi-layer tablet of which the layers are different in color, hue, luminance or the like from each other. Further, the present invention may be applied to a multi-layer tablet of which the layers are separated in a lateral direction rather than the vertical direction.

For control and determination of the tablet, the total weight of the tablet is predominantly considered. Numerical values of the total weight for the control are considered to be processed according to the following Table 1, because the content of the aspirin layer (average value of n tablets) in the tablet of which the ingredients are to be determined is obtained by a correlation coefficient between the total weight and area of the tablet (average values of n tablets) and the area of the aspirin layer (average value of n tablets). Also, in place of measuring the area of the whole tablet, the areas of both aspirin layer 204 and alkali layer 206 for image processing of the tablet may be detected, resulting in the determining of at least one layer, for example, the aspirin layer.

TABLE 1

| Detected Total Weight | Control Section of Tablet Machine |
| --- | --- |
| When total weight is above control range (any consecutive frequency or more) | Stopping of tabelt machine |
| When aspirin weight is above control range (any consecutive frequency or more) | Alarm |
| When total weight is beyond upper limit of control range ( ) | |
| (1) Aspirin content is within control range ( ) | Small decrease in alkali (-small movement) |
| (2) Aspirin content is beyond upper limit of control range ( ) | Large decrease in aspirin (−large movement) |
| (3) Aspirin content is below lower limit of control range ( ) | Large decrease in alkali (−large movement) |
| When total weight is below lower limit of control range ( ) | |
| (1) Aspirin content is within control range ( ) | Small increase in alkali (+small movement) |
| (2) Aspirin content is beyond upper limit of control range ( ) | Large increase in alkali (+large movement) |
| (3) Aspirin content is below lower limit of control range ( ) | Large increase in aspirin (+large movement) |
| When total weight is within control range ( ) | |
| (1) Aspirin content is within control range ( ) | No control |
| (2) Aspirin content is beyond upper limit of control range ( ) | Small decrease in aspirin (−small movement) |
| (3) Aspirin content is below lower limit of control range ( ) | Small increase in aspirin (+small movement) |

The amount of movement of the punches required for changing the amount of alkali is adjusted through two stages from the current control state of the tablet machine. (0.01 small movement large movement, 0.01 large movement 1) and (limit of the pestle position: 5.0-7.5) are prefereable. Also, the amount of movement of the punches required for changing the amount of asprin is adjusted through two stages from the current control state of one tablet machine. (0.01 small movement large movement, 0.01 large movement 0.05) and (limit of the pestle position: 4.0-5.5) are preferable.

Figure 15:
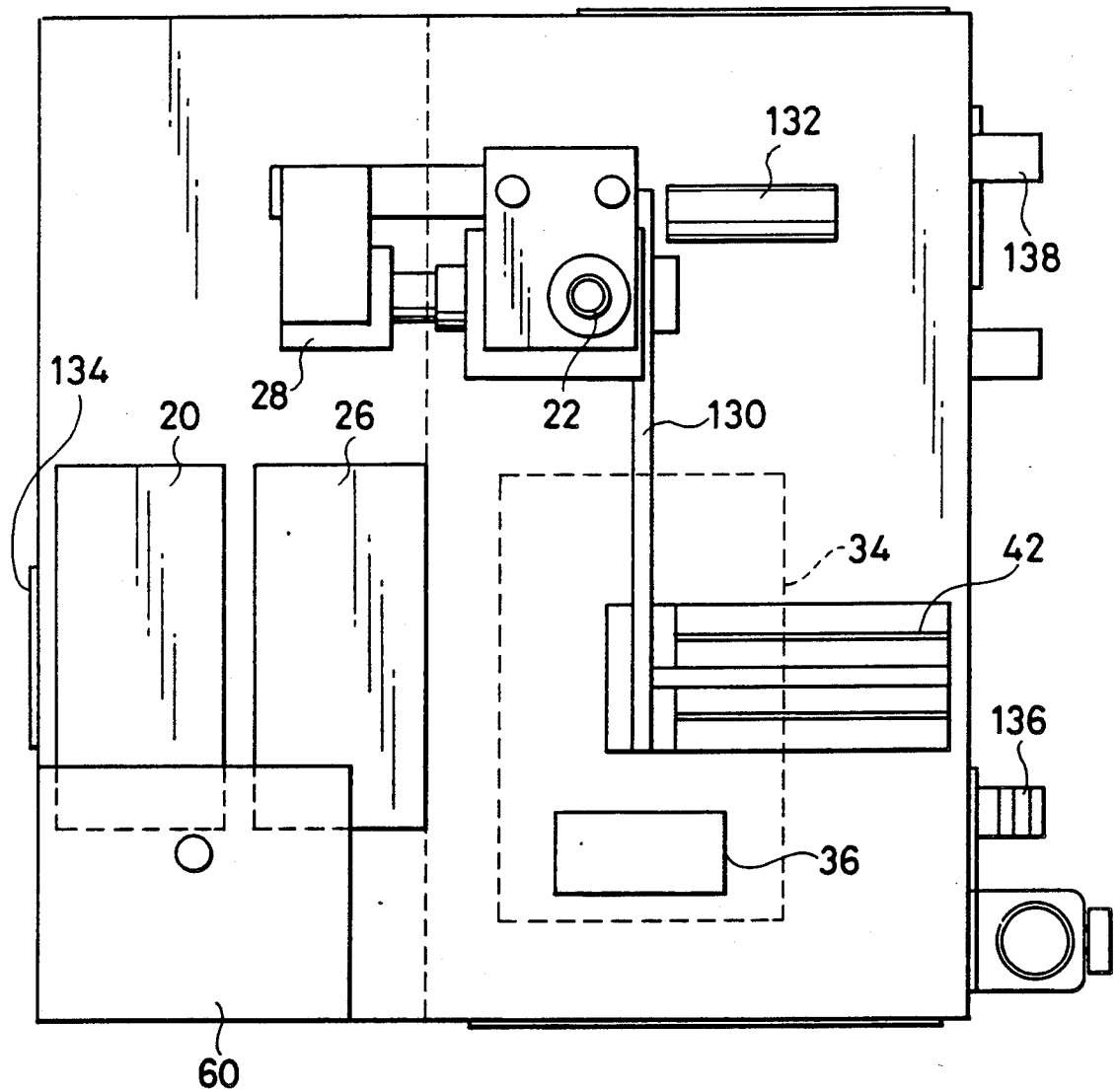
FIG. 15 is a plan view showing another embodiment of a tablet determining apparatus according to the present invention.
Figure 16:
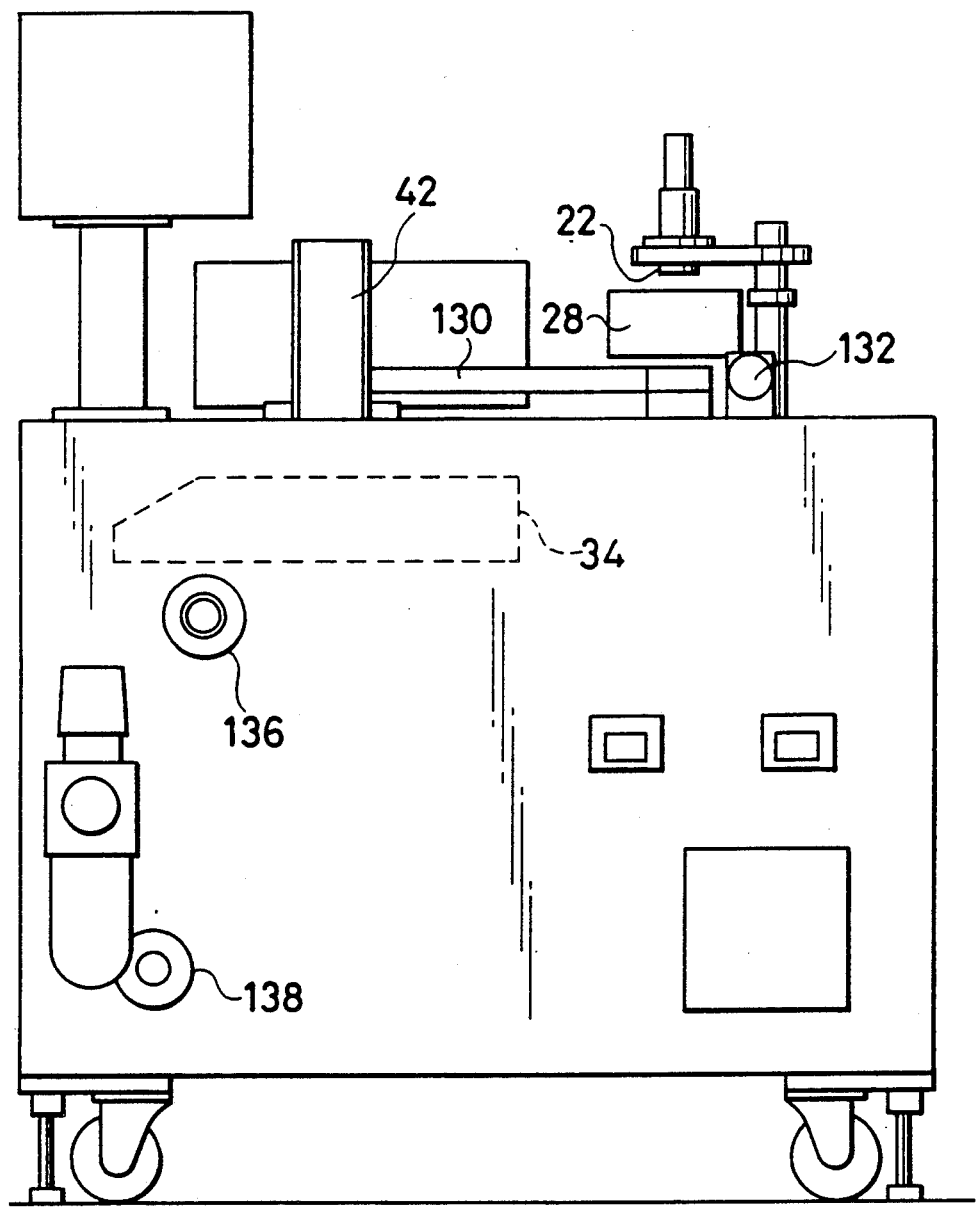
FIG. 16 is a side elevation view of the tablet determining apparatus shown in FIG. 15.

In another embodiment of the present invention shown in FIGS. 15 and 16, a tablet 200 is fed to an lighting tube 22 arranged opposite to a camera 28 through a tablet transfer mechanism 130 employing a belt conveyor line moved by means of a motor 132. The illustrated embodiment is also provided with an air blow structure comprising a propeller fan 134, a suction port 136 and an exhaust port 138.

Now, an example of preparation of a two-layer tablet will be detailedly described with reference to FIGS. 17A to 19C.

Figures 17A, 17B, 17C:
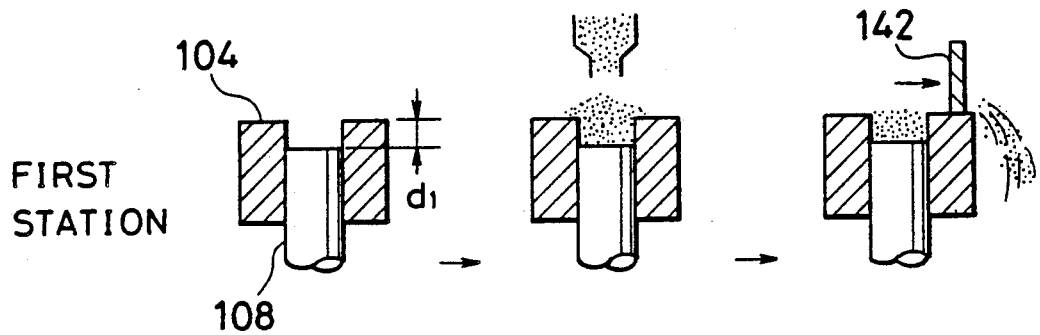
FIGS. 17A to 17C each are a schematic sectional view of a punch and die combination showing a first stage in the preparation of a two-layer tablet.

FIGS. 17A to 17C show the operation of a die and punch combination at a first stage of the tablet preparation, wherein the punch and die combination is charged with a first ingredient of a two-layer tablet. For this purpose, a lower punch 108 is first lowered to define a first depression of $d_1$ in depth in a die 104 and then the depression is filled with the first ingredient. Then, the excess of the first ingredient is removed by means of a scraper 142, resulting in the first ingredient being charged in a proper amount.

Figures 18A, 18B, 18C:
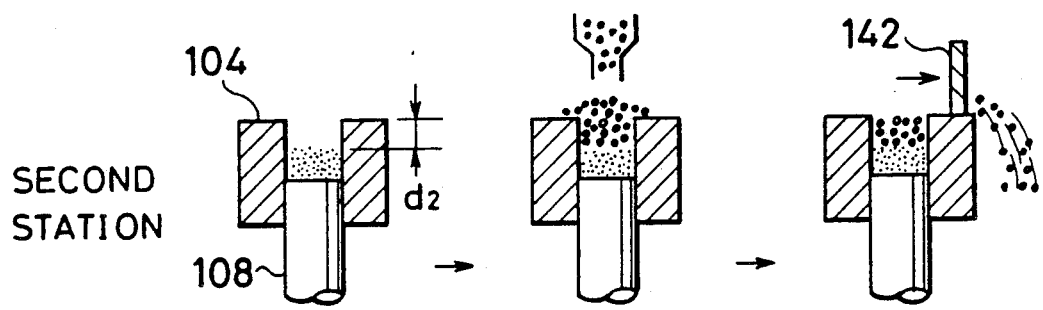
FIGS. 18A to 18C each are a schematic sectional view showing a second stage in the preparation of a two-layer tablet.

Subsequently, a second stage shown in FIGS. 18A to 18C is carried out. More particularly, the lower punch 108 is further lowered by a distance of $d_2$. At this time, the first ingredient may be lightly tamped by means of an upper punch 106. Then, a second ingredient of the tablet is charged in the die 104 and the excess of the second ingredient is removed by the scraper 142, so that the second ingredient may be charged in a proper amount.

Figures 19A, 19B, 19C:
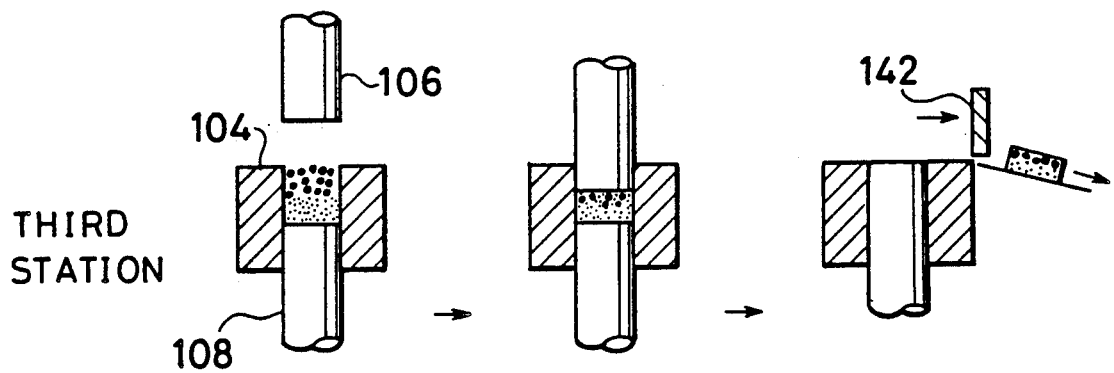
FIGS. 19A to 19C each are a schematic sectional view showing a third stage in the preparation of a two-layer tablet.

Thereafter, a third or final stage of the preparation takes place in such a manner as shown in FIGS. 19A to 19C. The charged first and second ingredients are tamped by the upper punch 106 to form a two-layer tablet as shown in FIGS. 19A and 19B, which is then discharged from the punch and die combination as shown in FIGS. 19C.

The amount of each of the first and second ingredients to be charged is controlled through a stroke of the lower punch 108 The amounts of the first and second ingredients are controlled by adjusting the distances $d_1$ and $d_2$, respectively The stroke of the lower punch 108 may be adjusted using any suitable means widely known in the art such as a combination of a pulse motor, a threaded screw and a nut.

As can be seen from the foregoing, the present invention is so constructed that a multi-layer tablet is lighted from the light sources, an area of the side surface of the tablet on which a boundary line between the layers appears is detected through the camera, an area of the side surface of at least one of the layers of the tablet which are separated by the boundary line is detected by image processing, and data obtained by the image processing and data on the total weight of the tablet are used for determining the layer by processing. Thus, the present invention permits ingredients of a multi-layer tablet to be accurately determined without breaking the tablet. Also, the above-described construction of the present invention not only ensures that the determination of the tablet can be continuously and automatically accomplished but significantly reduces the time required for the tablet determining operation.

While preferred embodiments of the invention have been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A method for determining the weight of a component layer of a tablet, the method comprising the steps of:

weighing a tablet to measure a weight $W_0$ of the tablet;

taking an image of the whole side surface of the tablet to measure a side surface area $A_0$ of the tablet;

taking an image of the side surface of a layer of at least one predetermined component of the tablet to measure a side surface area $A_1$ of the layer; and calculating a weight $W_1$ of the predetermined component according to a predetermined formula using the weight $W_0$, whole side surface area $A_0$ and side surface area $A_1$.

2. A method as defined in claim 1, wherein the image of the whole side surface of the tablet is taken by laterally lighting the side surface of the table.

3. A method as defined in claim 1 or 2, wherein the layer is translucent;

the image of the side surface of the layer being taken by vertically lighting the layer.

4. A method as defined in claim 3, wherein the lighting on said layer is carried out downwardly.

5. A method as defined in claim 1, wherein the formula is $$W_1 = B_0 + B_1 A_1 + B_2 A_0 + B_3 W_0$$

wherein $B_0$, $B_1$, $B_2$ and $B_3$ are parameters determined by a multiple regression analysis.

6. A method as defined in claim 1, further comprising the step of controlling the weight of components of tablets to be fed, depending upon the calculated weight of said predetermined component.

7. A method as defined in claim 6, wherein the amount of the predetermined component is controlled.

8. A method for determining the weight of a component layer of a tablet, said method comprising the steps of:

weighing a tablet to detect a weight $W_0$ of the tablet;

taking an image of a whole side surface of the tablet to measure a side surface area $A_0$ of the tablet;

taking an image of a side surface of a layer of at least one predetermined component of the tablet to measure a side surface area $A_1$ of the layer; and obtaining a weight $W_1$ of the predetermined component using the weight $W_0$, whole side surface area $A_0$ and side surface area $A_1$ by applying a formula $$W_1 = B_0 + B_1 A_1 + B_2 A_0 + B_3 W_0$$

wherein $B_0$, $B_1$, $B_2$ and $B_3$ are parameters determined by a multiple regression analysis.

9. A method for determining the weight of a component layer of a tablet, the method comprising the steps of:

weighing a tablet to detect a weight $W_0$ of the tablet;

taking an image of a whole side surface of the tablet to measure a side surface area $A_0$ of the tablet;

taking an image of a side surface of a layer of at least one predetermined component of the tablet to measure a side surface area $A_1$ of the layer;

obtaining a weight $W_1$ of the predetermined component according to a predetermined formula using the weight $W_0$, whole side surface area $A_0$ and side surface area $A_1$; and controlling the amount of the predetermined component of the tablet to be fed for preparing the tablet, depending upon the obtained weight of the predetermined component.

10. Apparatus for determining the weight of a component layer of a tablet, the apparatus comprising:

a weighing means for weighing a tablet to detect a weight $W_0$ of said tablet;

an image-taking means for taking an image of the whole side surface of said tablet to measure a side surface area $A_0$ of said tablet;

said image-taking means also taking an image of the side surface of a layer of at least one predetermined component of said tablet to measure a side surface area $A_1$ of said layer; and a processing means for obtaining a weight $W_1$ of said predetermined component according to a predetermined formula using said weight $W_0$, whole side surface area $A_0$ and side surface area $A_1$.

11. An apparatus as defined in claim 10, wherein said image of said whole side surface of said tablet is taken by laterally lighting the side surface of said table.

12. An apparatus as defined in claim 10 or 11, wherein said component layer is translucent;

said image of said side surface of said layer being taken by vertically lighting said layer.

13. An apparatus as defined in claim 12, wherein the lighting on said layer is carried out downwardly.

14. An apparatus as defined in claim 10, wherein said formula is $$W_1 = B_0 + B_1 A_1 + B_2 A_0 + B_3 W_0$$

wherein $B_0$, $B_1$, $B_2$ and $B_3$ are parameters determined by a multiple regression analysis.

15. An apparatus as defined in claim 10, further comprising a control means for controlling the amount of at least one component of tablets which are to be fed, depending upon the obtained weight of said predetermined component.

16. An apparatus as defined in claim 15, wherein the amount of said predetermined component is controlled.

17. An apparatus for determining the weight of a component layer of a tablet, the apparatus comprising:

a weighing means for weighing a tablet to detect a weight $W_0$ of said tablet;

an image-taking means for taking an image of the whole side surface of said tablet to measure a side surface area $A_0$ of said tablet;

said image-taking means also taking an image of the side surface of a layer of at least one predetermined component of said tablet to measure a side surface area $A_1$ of said layer; and a processing means for obtaining a weight $W_1$ of said predetermined component by using said weight $W_0$, whole side surface area $A_0$ and side surface $A_1$ and a formula $$W_1 = B_0 + B_1 A_1 + B_2 A_0 + B_3 W_0$$

wherein $B_0$, $B_1$, $B_2$ and $B_3$ are parameters determined by a multiple regression analysis.

18. An apparatus for determining the weight of a component layer of a tablet, the apparatus comprising:

a weighing means for weighing a tablet to detect a weight $W_0$ of the tablet;

an image-taking means for taking an image of the whole side surface of said tablet to measure a side surface area $A_0$ of said tablet;

said image-taking means also taking an image of the side surface of a layer of at least one predetermined component of said tablet to measure a side surface area $A_1$ of said layer; and a processing means for obtaining a weight $W_1$ of said predetermined component according to a predetermined formula using said weight $W_0$, whole side surface area $A_0$ and side surface area $A_1$; and a control means for controlling the amount of at least one component of said tablet to be fed depending upon the obtained weight of said predetermined component.

19. A method for determining the weight of a component of a tablet, said method comprising the steps of:

taking sample tablets;

determining a formula which relates total weights $W_0$, whole side surface areas $a_0$, and component side surface areas $a_1$ of the sample tablets to weights $w_1$ of components of the sample tablets;

taking a tablet for determination;

weighing the tablet for determination to detect a total weight $W_0$ of the tablet for determination;

taking an image of a whole side surface of the tablet for determination to measure a side surface area $A_0$ of the tablet for determination;

taking an image of a side surface of a layer of a component of the tablet for determination to measure a side surface area $A_1$ of the layer; and applying the formula to the measured values of $W_0$, $A_0$, and $A_1$ of the tablet for determination to determine the weight of the component of the tablet for determination.

20. The method of claim 19, further comprising the step of:

controlling the weight of components of tablets to be fed depending upon the determined weight of the component of the tablet for determination.

21. The method of claim 19 wherein the step of determining the formula further comprises:

weighing each sample tablet to detect a weight $W_0$ of each sample tablet;

taking an image of a whole side surface of each sample tablet to measure a side surface area $a_0$ of each sample tablet;

taking an image of a side surface of a layer of a component of each sample tablet to measure a side surface area $a_1$ of the layer;

weighing the component of each sample tablet to detect a weight $w_1$ of the component of each sample tablet;

determining values of parameters $B_0$, $B_1$, $B_2$, and $B_3$ of a regression formula $w_1 = B_0 + B_1 a_1 + B_2 a_0 + B_3 w_0$ by a multiple regression analysis applied to the data of the measured values of $w_0$, $a_0$, $a_1$, and $w_1$ for each sample tablet; and wherein the step of applying the formula to the measured values of $W_0$, $A_0$ and $A_1$ comprises the step of respectively substituting the measured values for $W_0$, $A_0$, and $A_1$ into the formula.

22. The method of claim 19, wherein the step of determining the formula further comprises the steps of applying a multiple regression analysis to each of the total weights $w_0$, each of the whole side surface area $a_0$, each of the component side surface areas $a_1$, and each of the component weights $w_1$ to determine the parameters $B_0$, $B_1$, $B_2$, and $B_3$.

* * * * *